(12) United States Patent
Gofman et al.

(10) Patent No.: US 6,442,339 B1
(45) Date of Patent: Aug. 27, 2002

(54) OPERATION OF HALOGEN LAMP FOR CURING OF MATERIAL

(75) Inventors: Igor Y. Gofman, Croton-on-Hudson, NY (US); Joseph G. Colombo, Lodi, NJ (US)

(73) Assignee: Coltene/Whaledent, Inc., Mahwah, NJ (US)

(*) Notice: Subject to any disclaimer, the term of this patent is extended or adjusted under 35 U.S.C. 154(b) by 0 days.

(21) Appl. No.: 09/848,969

(22) Filed: May 4, 2001

(51) Int. Cl.$^7$ .............................................. H05B 37/02
(52) U.S. Cl. ...................................... 392/407; 315/309
(58) Field of Search .................................. 392/407, 416, 392/418; 315/302, 291, 311, 309; 219/485, 505

(56) References Cited

U.S. PATENT DOCUMENTS

| | | | |
|---|---|---|---|
| 4,855,647 A | * 8/1989 | Schaller et al. | ......... 315/209 R |
| 5,343,122 A | * 8/1994 | Sugimori et al. | ....... 315/209 R |
| 5,471,129 A | * 11/1995 | Mann | .......................... 320/21 |
| 6,208,090 B1 | * 3/2001 | Skilskyj et al. | ............. 315/360 |
| 6,329,762 B1 | * 12/2001 | Goh | ............................ 315/224 |
| 6,356,040 B1 | * 3/2002 | Preis et al. | .................. 315/309 |

FOREIGN PATENT DOCUMENTS

| JP | 8-55686 | * 2/1996 |
|---|---|---|
| JP | 8-102371 | * 4/1996 |

* cited by examiner

Primary Examiner—John A. Jeffery
(74) Attorney, Agent, or Firm—Katten Muchin Zavis Rosenman

(57) ABSTRACT

A method and apparatus for curing dental material with radiation from a halogen lamp provides for a shifting of a spectrum of the radiation to a shorter wavelength for increased rate of curing by adjusting current flow within a heating element of the lamp. The current is applied over an interval of time for accomplishing the curing. Feedback and feedforward circuitry, operative with a control signal of a regulated power source to reduce voltage applied by the power source to the heating element during an initial portion of the interval of time, prior to obtaining an operating temperature of the heating element, to maintain an upper bound on the magnitude of the current applied to the heating element, thereby to the vivid unnecessary and operations of the heating element for increased operating lifetime of the lamp.

11 Claims, 3 Drawing Sheets

OPERATION OF HALOGEN LAMP FOR CURING OF MATERIAL

BACKGROUND OF THE INVENTION

This invention relates to operation of a halogen lamp in a dental curing process and, more particularly, to the obtaining of more power in a usefull spectral region without diminishing useful lifetime of the lamp.

A halogen lamp has a tungsten filament which is heated by electric current during operation of the lamp. The lamp's lifetime is based on the integrity of the filament. Once the filament burns out, the lamp no longer operates. While the lamp is operating, heat produced by electric current in the filament induces evaporation of the filament. Thus, the filament is continuously evaporating during operation of the lamp and, when the diameter of the filament reaches the critical point, the lamp burns out. A higher current flow in the filament results in a more rapid evaporation. Thus, during the start-up interval of the lamp, before the filament has attained its operating temperature, a much larger current flows with a resultant higher rate of evaporation.

In order to preserve the lifetime of a lamp having a tungsten filament during operation wherein the lamp may be turned on and off frequently, it is known to use a current limiter such as an NTC (negative temperature coefficient) thermistor to suppress the initial inrush current while providing negligible electrical resistance once the filament has heated to operating temperature. Unfortunately, such a current limiter develops significant heat after suppressing the initial inrush current, and requires a cool-town (recovery) time after power is removed from the lamp and prior to reactivation of the lamp. Due to the temperature dependent operating characteristic of the thermistor, the thermistor must be allowed to cool down in order to restore its resistance to the appropriate value for reactivation of the lamp. The cool-town time is approximately one minute. This presents an inconvenience in the situation wherein it is desired to turn the lamp off momentarily before reactivating the lamp. Also, the current limiter suffers from the disadvantage of dissipating some of the electric power which would otherwise be employed usefully in operation of the lamp.

In the use of a halogen lamp for curing dental material, it is advantageous to operate the lamp in a fashion which accelerates the rate of the curing. Thereby, the curing can be accomplished advantageously in a lesser amount of time. One way to accomplish this is to raise the operating voltage of the lamp, resulting in increased power dissipation in the lamp with increased light output. However, this introduces the disadvantage of reduced lifetime of the lamp. Another factor to consider in accelerating the curing process is the spectral distribution of light produced by the lamp. The curing process is accomplished best with a light wavelength of approximately 450 nm (nanometers). However, more than 95 percent of halogen lamp light, in the case of a typical halogen lamp heated by a tungsten filament, has a wavelength over 600 nm. Therefore, normal operation of a halogen lamp suffers from a lack of optimization of the spectral distribution of the light for use in the curing of dental material.

SUMMARY OF THE INVENTION

In view of the aforementioned disadvantages and problems, it is an object of the present invention to operate a halogen lamp in a manner which accomplishes a more rapid curing of dental material while substantially retaining the expected lifetime of the lamp. In accordance with a feature of the practice of the invention, it is recognized that the spectrum of light radiated by the lamp is dependent on the electrical voltage employed for exciting the lamp. Thus, an increase of the operating voltage by 10 percent shifts the color temperature to give a 6 percent color temperature rise, in the case of a typical halogen lamp heated by a tungsten filament. The increase of the operating voltage by 10 percent in this lamp also results in an increase of radiated light energy by 34 percent. The increase in color temperature is manifested by a shifting of the maximum spectral radiation output from longer wavelength toward shorter wavelength. In the case of the foregoing example, the spectrum shifting results in an additional 5 percent light output. While the increase in applied voltage provides the foregoing advantageous features in the operation of the lamp, it is noted that the increased voltage is accompanied by a disadvantage in that the foregoing 10 percent increase in the operating voltage results in a shortening of the lamp's life by 40 percent.

In accordance with the methodology and the apparatus of the invention, enhanced usage of the halogen lamp for the curing of dental material is obtained by increasing the voltage applied to the lamp to shift the spectrum and obtain better utilization of the frequency spectrum of the output light, and to increase intensity of the output light, while regulating the applied voltage for a gradual increase of the voltage at the time of initial turn on of the lamp so as to avoid the initial surge current with its associated rapid evaporation of the filament. The design lifetime of the lamp is retained because the loss in use of the lamp associated with the increased voltage is balanced by the improved utilization of the spectrum, and the avoidance of the initial surge current so as to maintain an upper bound on the magnitude of the current.

BRIEF DESCRIPTION OF THE DRAWING

The aforementioned aspects and other features of the invention are explained in the following description, taken in connection with the accompanying drawing figures wherein.

Identically labeled elements appearing in different ones of the figures refer to the same element but may not be referenced in the description for all figures.

DETAILED DESCRIPTION OF THE INVENTION

Figure 1:
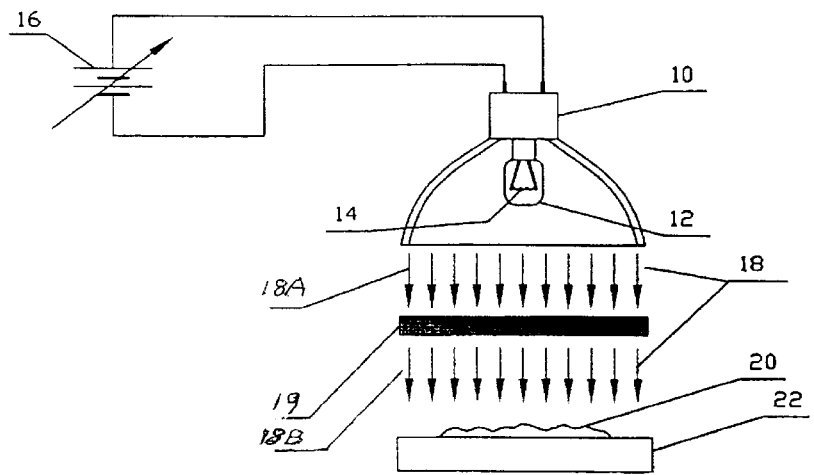
FIG. 1 shows a stylized view of a halogen lamp heated by an internal electrical filament, and radiating light useful in the curing of dental material.

With reference to FIG. 1, a halogen lamp 10 comprises an envelope 12 containing a halogen gas and enclosing a heating element in the form of an electrical filament 14 for heating the lamp 10. A source of electric power for the lamp 10 is represented by a variable voltage source, depicted as a variable battery 16, for applying voltage and current to the filament 14. Upon providing sufficient current by the battery 16 to heat the filament 14 to operating temperature of the lamp 10, the lamp 10 radiates light 18 through a filter 19 to illuminate dental material 20 held within a tray 22. The rays of the light 18 incident upon the filter 19 are further identified by the legend 1 8A, and the rays of the light 18 outputted by the filter 19 are further identified by the legend 18B. The filter 19 has a spectral passband of 300 nm to 600 nm. The filtered light 18B aids in the curing of the dental material 20. A higher intensity of the light 18 results in a decreased time to accomplish the curing. Also, an adjustment of the spectral distribution of the light 18 to provide increased intensity in the vicinity of 450 nm light wavelength results in a decreased time to accomplish the curing. Increased lifetime of the lamp 10 is accomplished by a gradual application of the excitation voltage to limit the magnitude of the heating current to the filament 14 as the electrical resistance of the filament 14 rises with the temperature of the filament 14.

The heating element has a resistance characterized by a positive temperature coefficient such that, at a relatively low temperature, the resistance is relatively low, and that at relatively high temperature, the resistance is relatively high, and wherein the resistance rises immediately after application of voltage to the heating element due to the rise in temperature of the heating element. By applying voltage of reduced magnitude during the initial stages of heating the filament, and allowing the voltage to rise in a manner substantially proportional to the resistance of the filament, the magnitude of the current is maintained substantially constant during the initial heating stage of the filament, thereby to place an upper bound on the magnitude of the current and to avoid the sudden inrush of current to the filament. This avoids unwanted evaporation of the filament to promote longevity in usage of the lamp. By use of the term "substantially proportional", it is to be understood that the applied voltage may not follow the changes in resistance exactly and that the relationship may not be perfectly linear. However, the voltage follows the resistance sufficiently closely to maintain an upper bound on the current.

Figure 2:
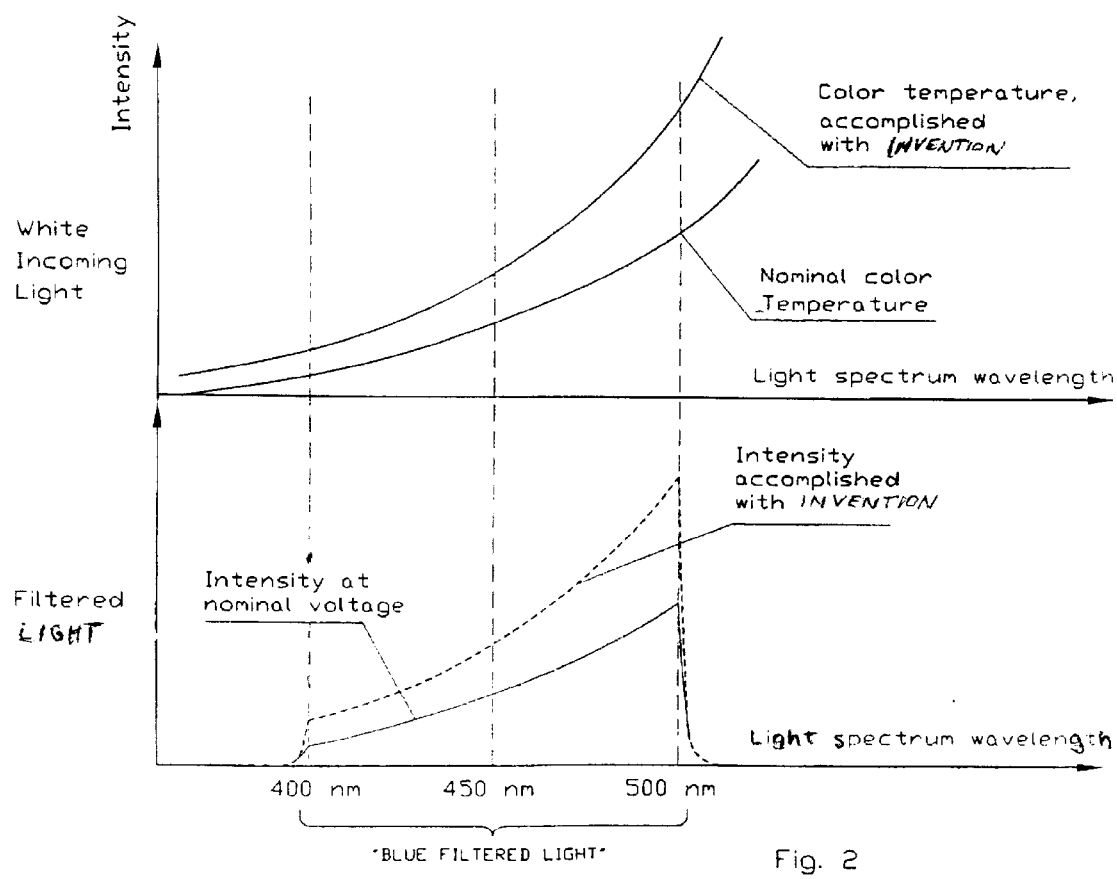
FIG. 2 provides two graphs representative of spectral emission characteristics of the halogen lamp as a function of voltage applied to the lamp filament, the upper graph being unfiltered light and the lower graph being filtered light.

In FIG. 2, the graph shows the intensity of light emitted by the lamp 10 as a function of frequency of the light. The intensity is shown along the vertical axis, and increasing wavelength is shown toward the right along the horizontal axis. For ease of reference, the light 18A incident upon the filter 19 is identified in FIG. 2 as white light, and the filtered light 18B outputted by the filter 19 is identified in FIG. 2 as blue light. In both the upper graph for the unfiltered light and the lower graph for the filtered light, there are two traces of which the lower trace represents the light output for normal energization of the lamp, and the upper trace represents the light output for excitation at increased current and voltage to the filament. The value of 450 nm is shown in the graph, and represents a preferred value of light wavelength for the curing of the dental material. It is noted that while the invention is being demonstrated for the case of the curing of dental material, the invention may be employed also for the processing of other material wherein the intensity and the spectral distribution of the radiation may be chosen to optimize the processing.

Figure 3:
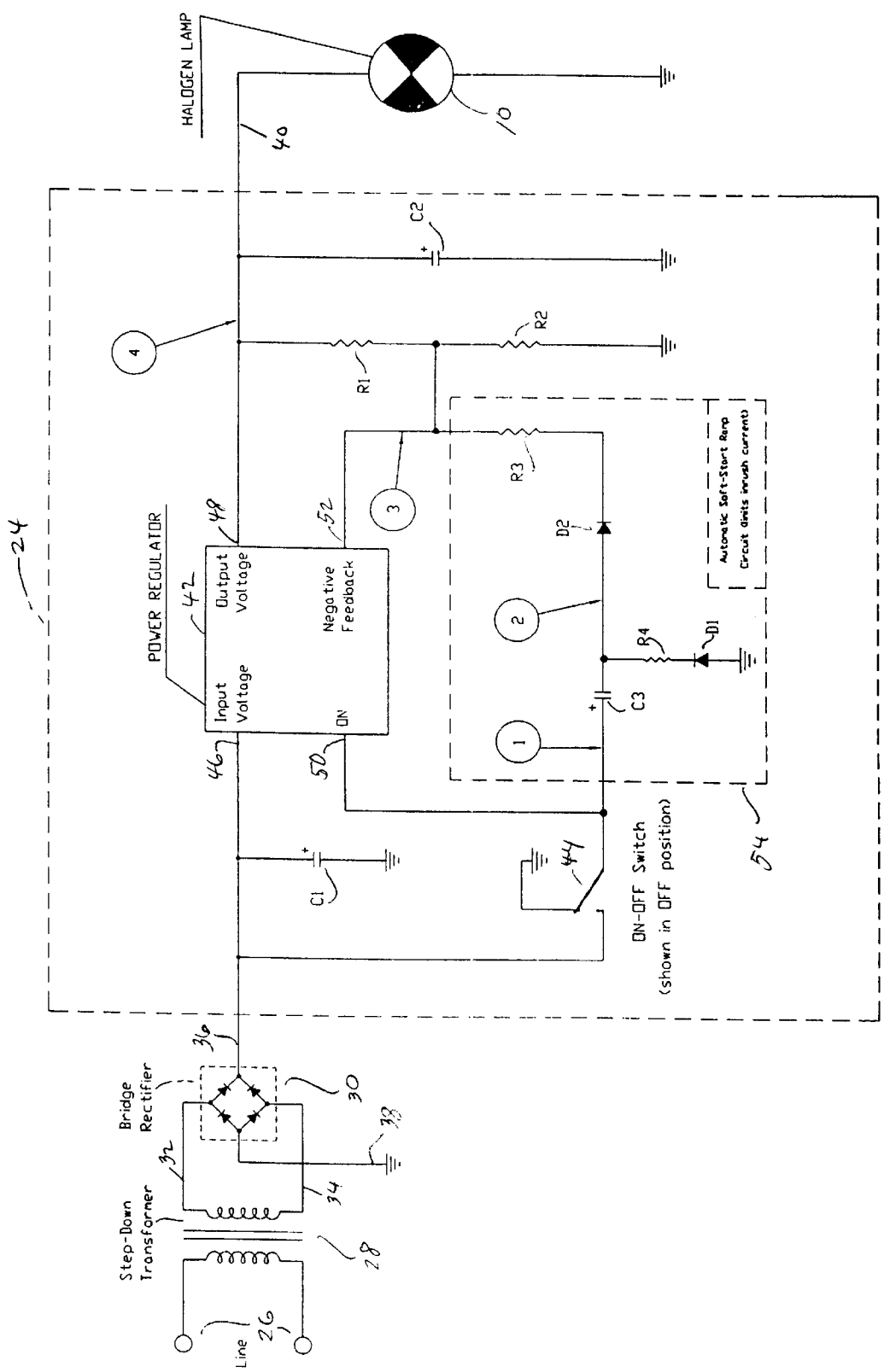
FIG. 3 is a diagram of an electric circuit for controlling voltage and current applied to the filament of the lamp in the practice of the invention.

FIG. 3 shows connection of a power source 24 to the halogen lamp 10. Input line voltage, such as that of the power provided to homes and offices, is applied by a terminal pair 26. Electric power at the terminal pair 26 is coupled by a step-down transformer 28 and a diode bridge rectifier 30 to the power source 24. The transformer 28 reduces the AC (alternating current) line voltage to a lower value of AC voltage across terminals 32 and 34 for driving the bridge rectifier 30. The AC voltage is converted by the bridge rectifier 30 to a DC (direct current) voltage appearing between line 36 and ground 38, the DC voltage being applied via line 36 and ground 38 to the power source 24. Voltage is outputted from the power source 24 to the halogen lamp 10 via line 40 and ground.

The power source 24 comprises a power regulator 42, three capacitors C1, C2 and C3, four resistors R1, R2, R3 and R4, two diodes D1 and D2, and a switch 44. The capacitor C1 connects between the line 36 and ground for filtering the input voltage on line 36. The capacitor C2 connects between line 40 and ground for filtering the output voltage on line 40. The input voltage on line 36 is applied to the first input voltage terminal 46 of the power regulator 42. The output voltage on line 40 is provided by an output voltage terminal 48 of the power regulator 42. A second input terminal 50 of the regulator 42 is responsive to a DC voltage, such as the voltage on line 36, to activate the regulator 42 to output the desired voltage on line 40; removal of the voltage from terminal 50 terminates the presence of the output voltage on line 40. Also included in the regulator 42 is a negative feedback terminal 52 by which operation of the regulator 42 is responsive to a feedback signal for maintaining the output voltage on line 40 at a desired value.

The resistors R1 and R2 are connected in series between line 40 and ground for providing a sample of the output voltage of line 40 at the junction between the resistors R1 and R2. The sample of the output voltage has a magnitude equal to only a fraction of the output voltage, and is applied, as feedback signal, to the feedback terminal 52 of the regulator 42. This constitutes a feedback circuit of the power source 24 for control of the magnitude of the output voltage on line 40. The magnitude of the feedback signal at terminal 52 establishes the magnitude of the voltage appearing on line 40. By way of example in the construction of the circuit, the resistors R1 and R2 are shown as fixed resistors wherein their values are selected to provide the desired output voltage. However, if desired, the voltage divider circuit of the resistors R1 and R2 may include a variable resistor (not shown) allowing for manual adjustment of the output voltage.

The switch 44 has two positions, a first position, as shown in FIG. 3, for grounding the second input terminal 50 of the regulator 42, and a second position in which the voltage of the line 36 is applied by the switch 44 to the second input terminal 50 of the regulator 42. In the first position of the switch 44, the regulator 42 is turned off so as to output no voltage on line 40 to the lamp 10. In the second position of the switch 44, the regulator 42 is turned on to output the voltage on line 40 for energizing the lamp 10.

A feedforward circuit 54 connects between the second input terminal 50 and the feedback terminal 52 of the regulator 42. The feedforward circuit 54 comprises the capacitor C3, the diodes D1 and D2, and the resistors R3 and R4. The feedforward circuit 54 is active immediately after the throwing of the switch 44 from the first position to the second position. The feedforward circuit 54 receives a step voltage upon the throwing of the switch 44 to its second position, and converts the step voltage to a ramp voltage which is applied to the feedback terminal 52. The ramp voltage initially is sufficiently great to overpower the feedback voltage provided by the resistors R1 and R2 so as to direct the regulator 42 to output a relatively low value of output voltage on line 40 to the lamp 10. As the ramp voltage decreases in magnitude, its effect is reduced so that the regulator 42 begins to increase the magnitude of the output voltage on line 40. At the conclusion of the ramp voltage, the operation of the regulator 42 is controlled only by the feedback voltage provided by the resistors R1 and R2 so that the full value of the desired output voltage appears on line 40.

In the operation of the feedforward circuit 54, the leading edge of the step voltage is coupled by the capacitor C3 to the diode D2, and then via the resistor R3 to the feedback terminal 52. The connection of the resistor R3 to the junction of the resistors R1 and R2 provides the configuration of a voltage divider which reduces the magnitude of the ramp voltage to a small fraction of the input voltage appearing on line 36. After the closure of the switch 44 to bring it into its second position, current flows through the capacitor C3, through the diode D2, and through the resistors R3 and R2 to ground, this current charging the capacitor C3 to produce an ever increasing voltage drop across the capacitor C3. The increasing voltage drop across the capacitor C3 results in a decreasing current through the capacitor C3 and the resistor R2 to provide the ramp voltage of decreasing amplitude at the feedback terminal 52. At the conclusion of the energization of the lamp 10, when the switch 44 is opened to bring it into its first position, the capacitor C3 discharges by current flow through a series circuit consisting of the diode D3, the resistor R4, the switch 44 and ground. The value of the resistor R4 is selected to provide for a discharge time which is sufficiently fast to ready the feedforward circuit 54 for the next interval of activation of the lamp 10.

Figure 4:
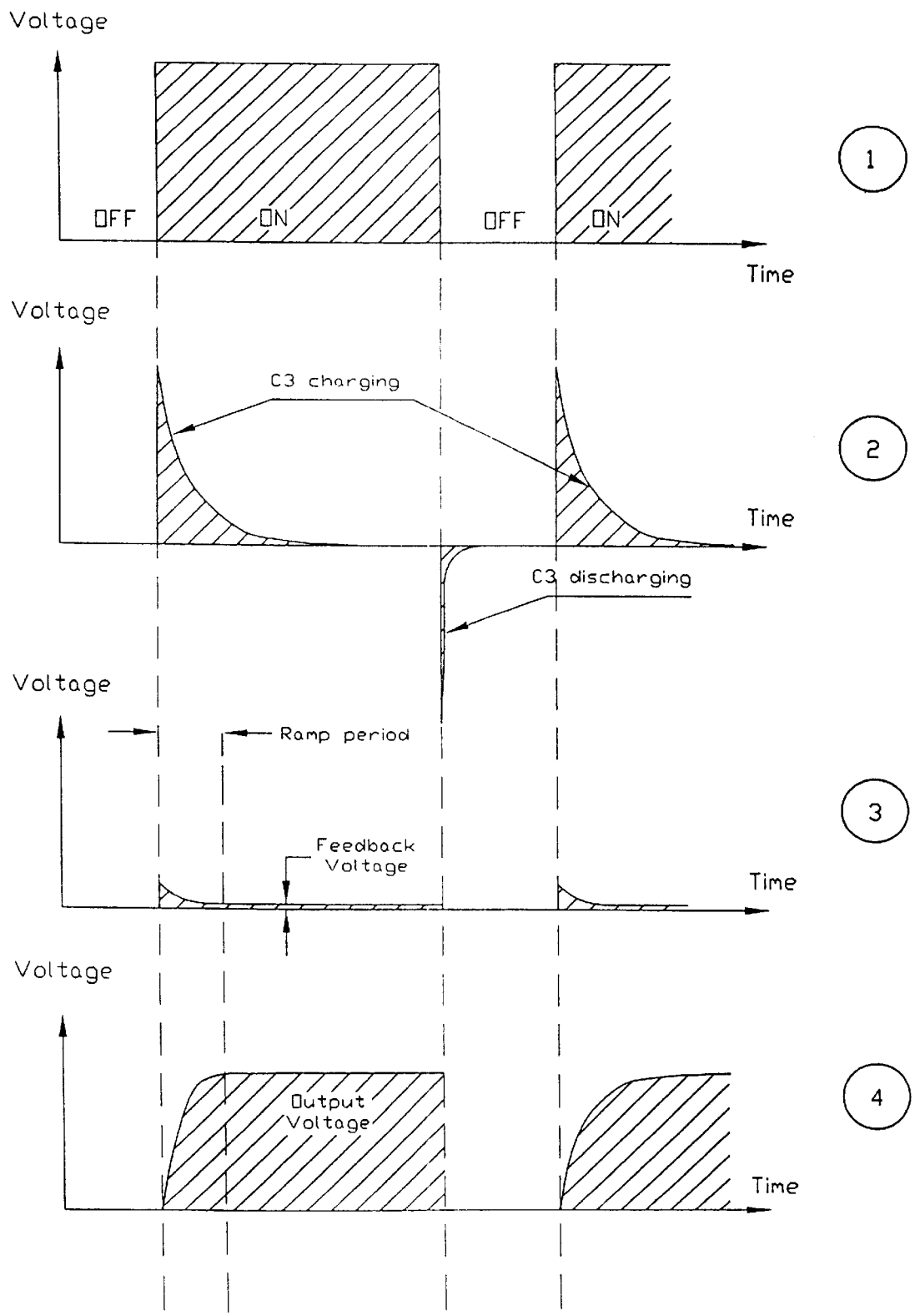
FIG. 4 is a set of graphs showing voltage as a function of time employed for heating the lamp filament.

In the set of graphs shown in FIG. 4 respective ones of the graphs are identified by the legends 1, 2, 3 and 4 which correspond to the numbering of selected nodes 1, 2, 3 and 4 in the circuitry of FIG. 3. Node 1 is at the junction of terminal 50, the switch 44, and capacitor C3. Node 2 is at the junction of the capacitor C3, resistor R4 and diode D2. Node 3 and is at the junction of terminal 52, resistor R3, resistor R1 and resistor R2. Node 4 is at the junction of terminal 48, the lamp 10, resistor R1 and capacitor C2. The first, the second, the third and the fourth graphs of FIG. 4 show the waveforms of the voltages appearing respectively at the nodes 1, 2, 3 and 4. In each of the four graphs, voltage is shown along the vertical axis, and increasing time is shown toward the right along the horizontal axis. The voltage waveforms shown in all of the four graphs are presented in time registration with each other.

With respect to the waveform at node 1, the voltage is zero when the node is grounded by the switch 44. When the circuitry is turned ON by movement of the switch 44 to the second position, the voltage is equal to the voltage on line 36 as is outputted by the diode bridge rectifier 30. These two voltage states are shown in the first graph.

With respect to the waveform at node 2, the voltage is proportional to the current flowing through the capacitor C3, wherein the waveform begins with the operation of the switch 44 to turn the circuitry to the ON state. The graph shows that, as the capacitor C3 charges, the current diminishes with time to approximate, during the initial stage of the charging, a ramp voltage. Eventually, the voltage passed by the capacitor C3 drops below the level necessary to keep the diode D2 in a state of conduction. From that point on, the ramp voltage no longer has an effect at node 3. The charging time is significantly less than the ON time of the switch 44.

With respect to the waveform at node 3, there is a scaling of the voltage waveform of the second node to reduce its value, and a summation of the voltage of the second node with the voltage produced by the voltage-divider circuit of resistors R1 and R2. Therefore, the initial stage (identified in FIG. 4 as the ramp period) of the voltage waveform at node 3 includes a ramp, while the balance of the waveform shows a voltage of substantially constant amplitude. The value of resistor R4 is much smaller than the value of the resistor R3 so that the discharging process of the capacitor C3 requires less time than the charging process.

With respect in the waveform at node 4 there is shown the voltage outputted to the lamp 10 by the regulator 42 in response to the voltage (at node 3) fed back to the feedback terminal 52. During the interval of time identified in FIG. 4 as the ramp period, there is a gradual rise in the amplitude of the voltage fed to the lamp 10 to provide a desired "soft" start which avoids a heavy inrush current to the lamp 10. Thereafter, the voltage fed to the lamp 10 has a constant amplitude until the throwing of the switch 44 to the OFF state wherein node 1 is grounded. Thereupon, the regulator 42 terminates the voltage fed to the lamp 10.

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

What is claimed is:

1. A method of curing material with radiation from a halogen lamp, comprising the steps of:

shifting the spectrum of the radiation to a wavelength for increased rate of curing, said shifting step including a step of adjusting current flow within a heating element of the lamp;

applying the current over an interval of time for accomplishing the curing of the material; and reducing voltage applied by a source of power to the heating element during an initial portion of the interval of time, prior to obtaining an operating temperature of the heating element, to maintain an upper bound on the magnitude of the current applied to the heating element, the upper bound on the current increasing the operating lifetime of the lamp.

2. A method according to claim 1, wherein the shifting of the spectrum shifts the spectrum to a shorter wavelength, and wherein the step of current adjusting provides for an increased flow of current resulting in an increased intensity of radiation produced by the lamp, the material being dental material.

3. A method according to claim 1, wherein the heating element is a filament having a resistance characterized by a positive temperature coefficient such that, at a relatively low temperature, the resistance is relatively low, and that at relatively high temperature, the resistance is relatively high, and wherein the resistance rises during said initial portion of the time interval, said voltage reducing step providing for a voltage substantially proportional to the resistance of the filament.

4. A method according to claim 1, wherein the source of power includes a power regulator outputting a voltage having a magnitude responsive to a control signal, and wherein said voltage reducing step is accomplished by altering the control signal during said initial portion of the time interval.

5. A method according to claim 4, wherein said power source includes a feedback circuit providing said control signal, and a feedforward circuit active during said initial portion of the time interval to override the feedback circuit for altering the value of the control signal by a ramp signal of decreasing amplitude.

6. A method of initiating and terminating radiation from a halogen lamp while maintaining an upper bound on the magnitude of current energizing the lamp, comprising the steps of:

applying the current to a heating element within the lamp over an interval of time for providing the radiation; and reducing voltage applied by a source of power to the heating element during an initial portion of the interval of time, prior to obtaining an operating temperature of the heating element, to maintain the upper bound on the magnitude of the current applied to the heating element, the upper bound on the current increasing the operating lifetime of the lamp;

wherein the source of power includes a power regulator outputting a voltage having a magnitude responsive to a control signal, and wherein said voltage reducing step is accomplished by altering the control signal during said initial portion of the time interval.

7. A method according to claim 8, wherein the heating element is a filament having a resistance characterized by a positive temperature coefficient such that, at a relatively low temperature, the resistance is relatively low, and that at relatively high temperature, the resistance is relatively high, and wherein the resistance rises during said initial portion of the time interval, said voltage reducing step providing for a voltage substantially proportional to the resistance of the filament.

8. A method of initiating and terminating radiation from a halogen lamp while maintaining an upper bound on the magnitude of current energizing the lamp, comprising the steps of:

applying the current to a heating element within the lamp over an interval of time for providing the radiation; and reducing voltage applied by a source of power to the heating element during an initial portion of the interval of time, prior to obtaining an operating temperature of the heating element, to maintain the upper bound on the magnitude of the current applied to the heating element, the upper bound on the current increasing the operating lifetime of the lamp;

wherein the source of power includes a power regulator outputting a voltage having a magnitude responsive to a control signal provided by a feedback circuit, and wherein said voltage reducing step is accomplished by a feedforward circuit active during said initial portion of the time interval to override the feedback circuit for altering the value of the control signal by a ramp signal of decreasing amplitude.

9. Apparatus to for initiating and terminating radiation from a halogen lamp while maintaining an upper bound on the magnitude of current energizing the lamp, comprising:

a power source for applying the current to a heating element within the lamp over an interval of time for providing the radiation; and control circuitry for reducing voltage applied by said power source to the heating element during an initial portion of the interval of time, prior to obtaining an operating temperature of the heating element, to maintain the upper bound on the magnitude of the current applied to the heating element, the upper bound on the current increasing the operating lifetime of the lamp.

wherein said power source includes a power regulator outputting a voltage having a magnitude responsive to a control signal, and wherein said control circuit includes a feedforward circuit operative to alter the control signal during said initial portion of the time interval.

10. Apparatus according to claim 9, wherein the heating element is a filament having a resistance characterized by a positive temperature coefficient such that, at a relatively low temperature, the resistance is relatively low, and that at relatively high temperature, the resistance is relatively high, and wherein the resistance rises during said initial portion of the time interval, said control circuitry providing for a voltage substantially proportional to the resistance of the filament.

11. Apparatus according to claim 9, wherein said control circuit includes a feedback circuit providing said control signal, and said feedforward circuit is active during said initial portion of the time interval to override the feedback circuit for altering the value of the control signal by a ramp signal of decreasing amplitude.

* * * * *